United States Patent [19]
Zepeda et al.

[11] Patent Number: 6,090,105
[45] Date of Patent: Jul. 18, 2000

[54] MULTIPLE ELECTRODE ABLATION APPARATUS AND METHOD

[75] Inventors: John Zepeda, Los Altos; Chaya Hirsch, Palo Alto; Kee Lee, Daly City; Edward J. Gough, Menlo Park, all of Calif.

[73] Assignee: Rita Medical Systems, Inc., Mountain View, Calif.

[21] Appl. No.: 08/971,415

[22] Filed: Nov. 17, 1997

Related U.S. Application Data

[63] Continuation-in-part of application No. 08/515,379, Aug. 15, 1995, Pat. No. 5,683,384.

[51] Int. Cl.$^7$ ................................................. A61B 17/39
[52] U.S. Cl. ........................... 606/41; 607/101; 607/102
[58] Field of Search ........................... 606/41, 42, 45–50; 607/100–102, 115, 116; 604/114

[56] References Cited

U.S. PATENT DOCUMENTS

| | | |
|---|---|---|
| Re. 32,057 | 12/1985 | Leveen . |
| Re. 32,066 | 1/1986 | Leveen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | Leveen . |
| 4,011,872 | 3/1977 | Komiya . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 566 450B1 | 10/1993 | European Pat. Off. . |
| 0 608 609 | 8/1994 | European Pat. Off. . |
| 2 283 701 | 4/1976 | France . |
| 2 670 664 | 6/1992 | France . |
| 10 07 960 | 10/1957 | Germany . |
| 21 24 684 | 11/1973 | Germany . |
| 89 09 492 U | 3/1990 | Germany . |
| 38 38 840 | 5/1990 | Germany . |
| 39 30 451 | 3/1991 | Germany . |
| 41 00 422 | 7/1992 | Germany . |
| 63-275632 | 11/1988 | Japan . |
| 2-121675 | 5/1990 | Japan . |
| WO 92/10142 | 6/1992 | WIPO . |
| WO 94/04220 | 3/1994 | WIPO . |
| WO 94/10925 | 5/1994 | WIPO . |
| WO 94/11059 | 5/1994 | WIPO . |
| WO 94/17856 | 8/1994 | WIPO . |
| WO 94/25110 | 11/1994 | WIPO . |
| WO 94/26178 | 11/1994 | WIPO . |
| WO 95/19142 | 7/1995 | WIPO . |
| WO 95/25471 | 9/1995 | WIPO . |
| WO 96/04860 | 2/1996 | WIPO . |
| WO 96/29946 | 10/1996 | WIPO . |
| WO 97/06739 | 2/1997 | WIPO . |

*Primary Examiner*—Michael Peffley
*Attorney, Agent, or Firm*—Wilson Sonsini Goodrich & Rosati

[57] ABSTRACT

An ablation apparatus includes an introducer with a distal end sufficiently sharp to penetrate tissue. An energy delivery device is configured to be coupled to an energy source. The energy delivery device includes a first electrode and a second electrode each with a tissue piercing distal portion. The first and second electrodes are at least partially positionable in the introducer and deployable from the introducer at a selected tissue site to an expanded state. In the expanded state the deployed first and second electrodes distend laterally away from the introducer with a radius of curvature to form a shaped array of deployed electrodes at the tissue site when positioned at the selected tissue site. The first electrode distal portion and the second electrode distal portion are each at least partially made of a shaped memory alloy material that displays stress induced martensite behavior above body temperature. A cable couples the energy source to the energy delivery device.

48 Claims, 10 Drawing Sheets

U.S. PATENT DOCUMENTS

| | | |
|---|---|---|
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |
| 4,080,959 | 3/1978 | Leveen . |
| 4,085,756 | 4/1978 | Weaver . |
| 4,095,602 | 6/1978 | Leveen . |
| 4,119,102 | 10/1978 | Leveen . |
| 4,121,592 | 10/1978 | Whalley . |
| 4,140,130 | 2/1979 | Storm, III . |
| 4,154,246 | 5/1979 | Leveen . |
| 4,230,129 | 10/1980 | Leveen . |
| 4,237,898 | 12/1980 | Whalley . |
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,992 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | Deluca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | Leveen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Van't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | Leveen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |

| | | |
|---|---|---|
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |
| 5,293,869 | 3/1994 | Edwards et al. . |
| 5,295,955 | 3/1994 | Rosen et al. . |
| 5,300,068 | 4/1994 | Rosar et al. . |
| 5,300,069 | 4/1994 | Hunsberger et al. . |
| 5,300,099 | 4/1994 | Rudie . |
| 5,304,214 | 4/1994 | Deford et al. . |
| 5,309,910 | 5/1994 | Edwards et al. . |
| 5,313,943 | 5/1994 | Housar et al. . |
| 5,314,466 | 5/1994 | Stern et al. . |
| 5,322,503 | 6/1994 | Desai . |
| 5,328,467 | 7/1994 | Edwards et al. . |
| 5,334,193 | 8/1994 | Nardella . |
| 5,334,206 | 8/1994 | Daikuzono . |
| 5,336,222 | 8/1994 | Durgin, Jr. et al. . |
| 5,342,357 | 8/1994 | Nardella . |
| 5,348,554 | 9/1994 | Imran et al. . |
| 5,354,296 | 10/1994 | Turkel . |
| 5,363,861 | 11/1994 | Edwards et al. . |
| 5,365,926 | 11/1994 | Desai . |
| 5,366,490 | 11/1994 | Edwards et al. . |
| 5,368,592 | 11/1994 | Stern et al. . |
| 5,370,675 | 12/1994 | Edwards et al. ............... 607/101 |
| 5,370,678 | 12/1994 | Edwards et al. . |
| 5,383,876 | 1/1995 | Nardella . |
| 5,383,917 | 1/1995 | Desai et al. ............... 607/102 |
| 5,385,544 | 1/1995 | Edwards et al. . |
| 5,397,339 | 3/1995 | Desai . |
| 5,398,683 | 3/1995 | Edwards et al. . |
| 5,401,272 | 3/1995 | Perkins . |
| 5,403,311 | 4/1995 | Abele et al. . |
| 5,405,346 | 4/1995 | Grundy et al. . |
| 5,409,453 | 4/1995 | Lundquist et al. . |
| 5,411,025 | 5/1995 | Webster, Jr. . |
| 5,417,687 | 5/1995 | Nardella . |
| 5,421,819 | 6/1995 | Edwards et al. . |
| 5,423,807 | 6/1995 | Milder . |
| 5,423,808 | 6/1995 | Edwards et al. . |
| 5,423,811 | 6/1995 | Imran et al. . |
| 5,433,708 | 7/1995 | Nichols et al. . |
| 5,435,805 | 7/1995 | Edwards et al. . |
| 5,437,662 | 8/1995 | Nardella . |
| 5,437,664 | 8/1995 | Cohen et al. . |
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,462,521 | 10/1995 | Brucker et al. . |
| 5,470,308 | 11/1995 | Edwards et al. . |
| 5,470,309 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,500,012 | 3/1996 | Brucker et al. . |
| 5,505,730 | 4/1996 | Edwards . |
| 5,507,743 | 4/1996 | Edwards et al. . |
| 5,509,419 | 4/1996 | Edwards et al. . |
| 5,514,130 | 5/1996 | Baker . |
| 5,514,131 | 5/1996 | Edwards . |
| 5,520,684 | 5/1996 | Imran . |
| 5,531,676 | 7/1996 | Edwards et al. . |
| 5,531,677 | 7/1996 | Lundquist et al. . |
| 5,536,240 | 7/1996 | Edwards et al. . |
| 5,536,267 | 7/1996 | Edwards et al. . |
| 5,540,655 | 7/1996 | Edwards et al. . |
| 5,542,915 | 8/1996 | Edwards et al. . |
| 5,542,916 | 8/1996 | Hirsch et al. . |
| 5,542,928 | 8/1996 | Evans et al. . |
| 5,545,161 | 8/1996 | Imran . |
| 5,545,171 | 8/1996 | Sharkey et al. . |
| 5,545,193 | 8/1996 | Fleischman et al. . |
| 5,545,267 | 8/1996 | Frederiksen et al. . |
| 5,548,597 | 8/1996 | Edwards et al. . |
| 5,549,108 | 8/1996 | Edwards et al. . |
| 5,549,644 | 8/1996 | Lindquist et al. . |
| 5,554,110 | 9/1996 | Edwards et al. . |
| 5,556,377 | 9/1996 | Rosen et al. . |
| 5,558,672 | 9/1996 | Edwards et al. . |
| 5,558,673 | 9/1996 | Edwards et al. . |
| 5,560,358 | 10/1996 | Arnold et al. . |
| 5,562,703 | 10/1996 | Desai . |
| 5,599,345 | 2/1997 | Edwards et al. . |
| 5,599,346 | 2/1997 | Edwards et al. . |
| 5,609,151 | 3/1997 | Mulier et al. . |
| 5,620,481 | 4/1997 | Desai et al. . |
| 5,817,092 | 10/1998 | Behl ............... 606/41 |
| 5,827,276 | 10/1998 | LeVeen et al. ............... 606/41 |

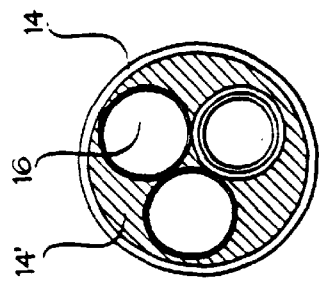
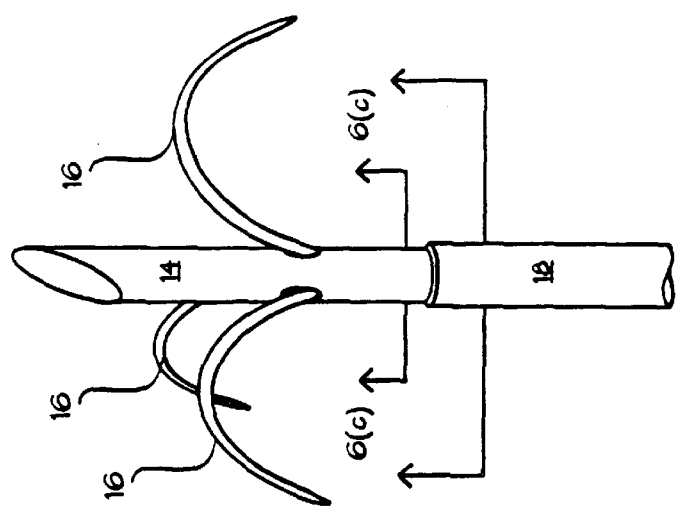
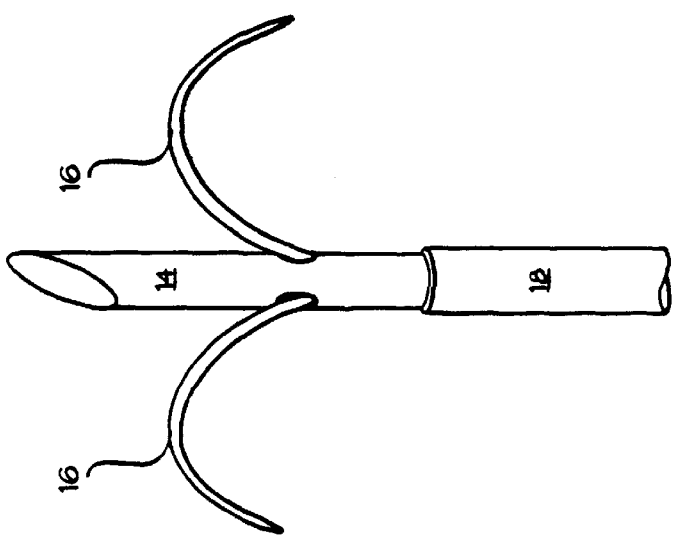

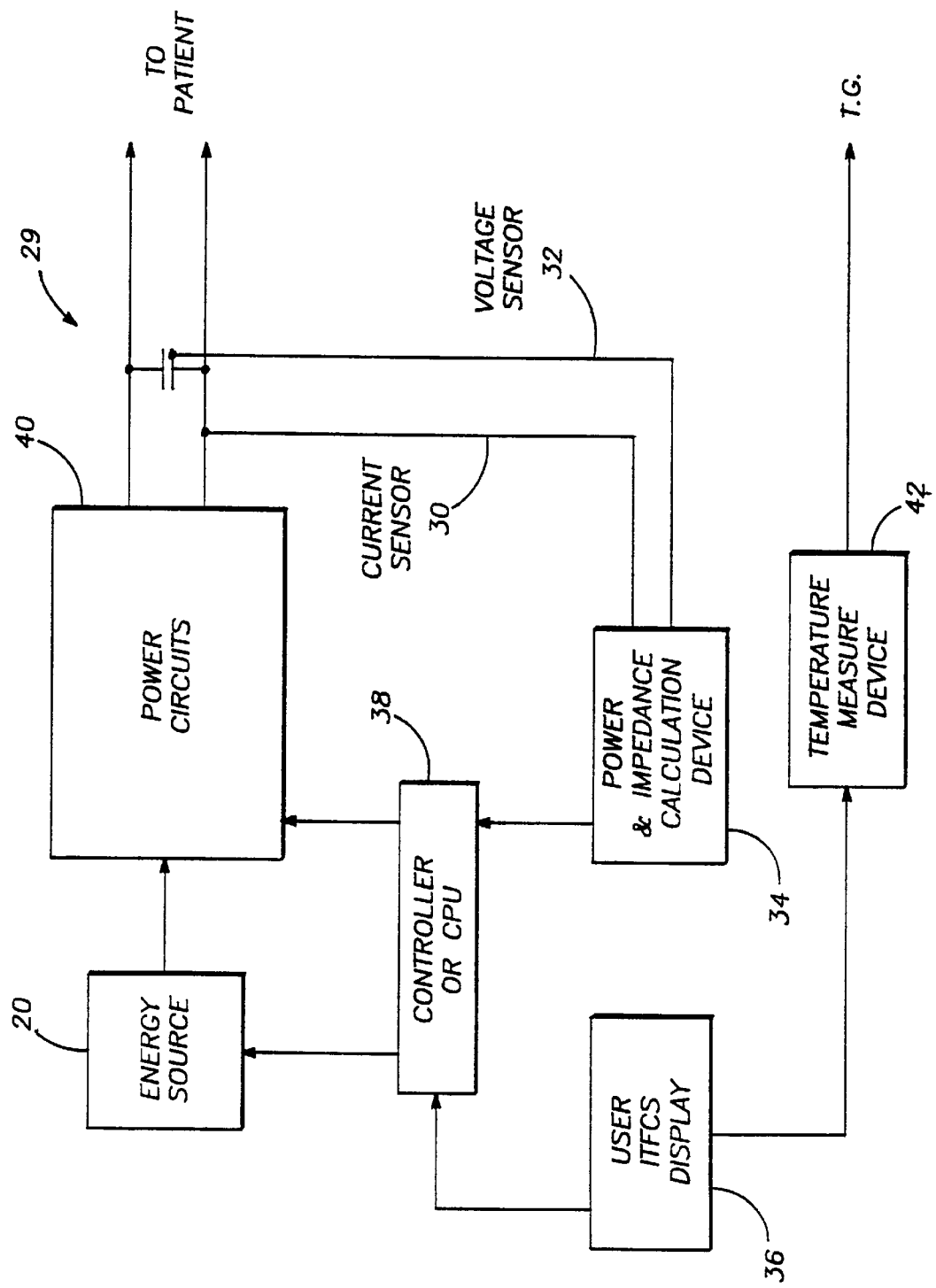

MULTIPLE ELECTRODE ABLATION APPARATUS AND METHOD

REFERENCE TO RELATED APPLICATION

This application is a continuation-in-part of U.S. patent application Ser. No. 08/515,379, filed Aug. 15, 1995, now U.S. Pat. No. 5,683,384 entitled "Multiple Antenna Ablation Apparatus", incorporated herein by reference.

BACKGROUND OF THE INVENTION

1. Field of the Invention

This invention relates generally to an ablation apparatus with an introducer electrode and a plurality of electrodes, each having a distal portion made of a shaped memory material that exhibits stress induced martensite behavior above body temperature.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. No. 4,562,200; U.S. Pat. No. 4,411,266; U.S. Pat. No. 4,838,265; U.S. Pat. No. 5,403,311; U.S. Pat. No. 4,011,872; U.S. Pat. No. 5,385,544; and U.S. Pat. No. 5,385,544.

There is a need for a multiple electrode ablation method and apparatus where at least a portion of the distal portions of the electrodes are made of a shaped memory alloy material that exhibits stress induced martensite behavior above body temperature.

SUMMARY OF THE INVENTION

Accordingly, it is an object of the invention is to provide an ablation device and method which provides selective ablation of targeted tissue sites.

Another object of the invention is to provide a method and apparatus that provides ablation of tumors.

Yet another object of the invention is to provide a method and apparatus which uses electrodes that are positionable in an introducer and distend away from the introducer and come back on themselves in order to surround a selected ablation mass.

Another object of the invention is to provide a method and an ablation device with a introducer electrode that pierces and advances through tissue, secondary electrodes positionable in the introducer electrode, where the secondary electrodes are deployed and extend away from the introducer electrode, and the secondary electrodes are formed of a shaped memory alloy material which exhibits stress induced martensite behavior above body tempeature.

These and other objectives are achieved in an ablation apparatus including an introducer with a distal end sufficiently sharp to penetrate tissue. An energy delivery device is configured to be coupled to an energy source. The energy delivery device includes a first electrode and a second electrode each with a tissue piercing distal portion. The first and second electrodes are at least partially positionable in the introducer and deployable from the introducer at a selected tissue site to an expanded state. In the expanded state the deployed first and second electrodes distend laterally away from the introducer with a radius of curvature to form a shaped array of deployed electrodes at the tissue site when positioned at the selected tissue site. The first electrode distal portion and the second electrode distal portion are each at least partially made of a shaped memory alloy material that displays stress induced martensite behavior above body temperature. A cable couples the energy source to the energy delivery device.

In another embodiment, a method for creating an ablation volume in a selected tissue mass advances the introducer through tissue to the selected tissue site. Energy is applied to the first and second electrode distal portions while they are positioned in the introducer. A stress induced martensitic state in the first and second electrodes at a temperature above body temperature. The first and second electrodes are advanced from the introducer to surround a selected tissue mass. Energy is delivered from the energy source to the first and second electrodes. An ablation volume is created in the selected tissue mass.

BRIEF DESCRIPTION OF THE FIGURES

FIG. 7(a) is a perspective view of the multiple electrode ablation apparatus of the present invention illustrating two secondary electrodes which provide a retaining and gripping function.

FIG. 7(b) is a perspective view of the multiple electrode ablation apparatus of the present invention illustrating three secondary electrodes which provide a retaining and gripping function.

FIG. 7(c) is a cross-sectional view of the apparatus of FIG. 7(b) taken along the lines 6(c)—6(c).

FIG. 10 is a block diagram illustrating the inclusion of a controller, energy source and other electronic components of the present invention.

DETAILED DESCRIPTION

Figure 1:
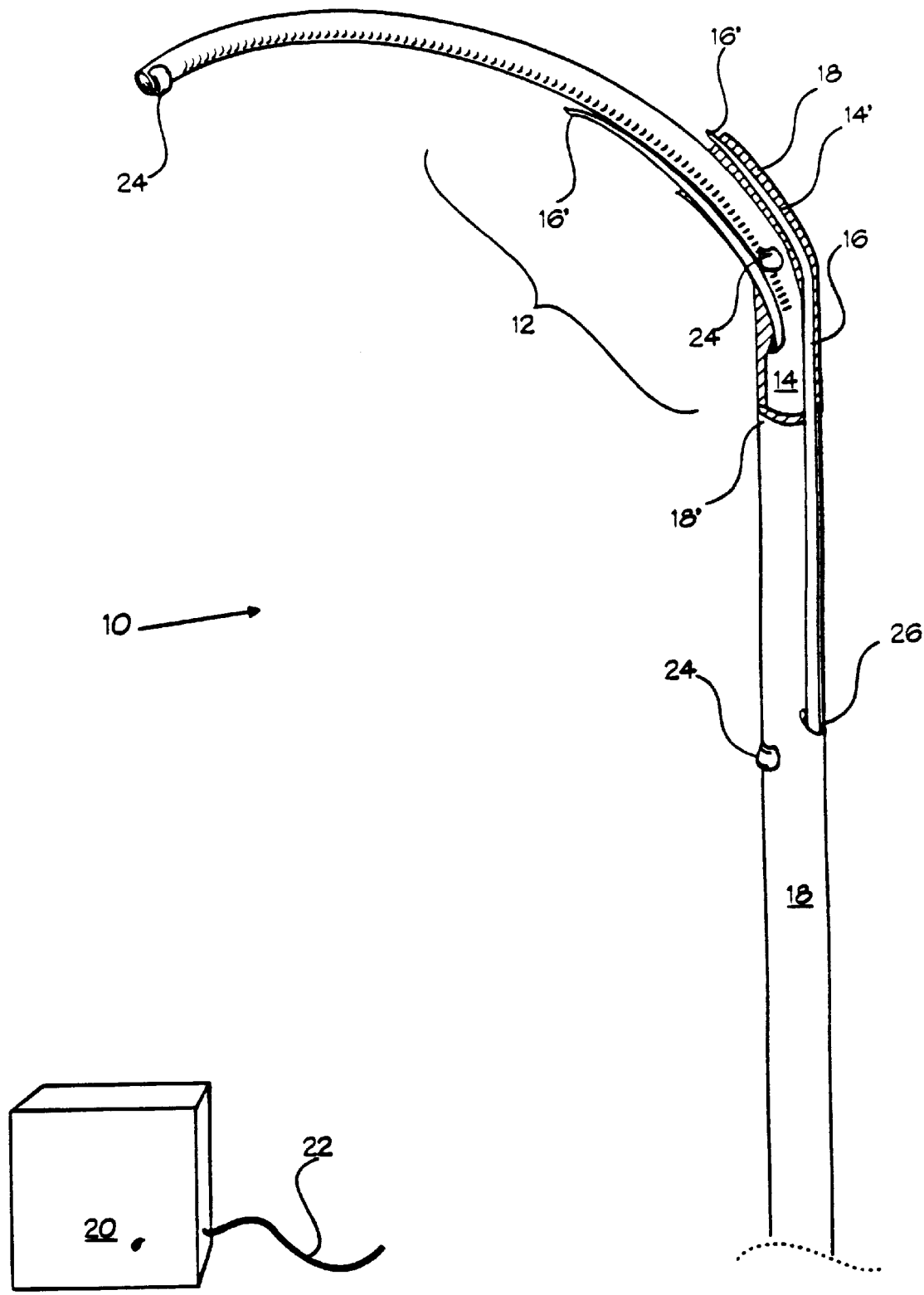
FIG. 1 is a perspective view of the multiple electrode ablation apparatus of the present invention illustrating an introducer electrode and a single laterally deployed secondary electrode.

As shown in FIG. 1, an ablation treatment apparatus 10 includes a multiple electrode device 12. Multiple electrode device 12 includes an introducer electrode 14, and one or more secondary electrodes 16. Secondary electrodes 16 are positionable in an introducer electrode lumen before or after the introduction of introducer electrode 14 through tissue. When introducer electrode 14 reaches a selected tissue ablation site in a selected tissue mass, including but not limited to a solid lesion, secondary electrodes 16 are laterally deployed from the introducer electrode lumen and into the selected tissue mass. Ablation proceeds from the interior of the selected tissue mass in a direction towards a periphery of the selected tissue mass.

Introducer electrode and secondary electrode 14 and 16 have an exterior ablation surface which delivers electromagnetic energy to the selected tissue mass. The length and size of each ablation surface can be variable. The length of introducer electrode ablation surface relative to secondary electrode ablation surface can be 20% or greater, 33 and ⅓% or greater, 50% or greater, 75% or greater, about the same length, or greater than the length of secondary electrode ablation surface. Lengths of introducer electrode and secondary electrodes 14 and 16 can be adjustable. Introducer electrode 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. The ablation can be between the ablation surfaces of introducer electroder and secondary electrodes 14 and 16 when operated in a monopolar mode with a ground pad.

Introducer electrode 14 is constructed so that it can be introduced percutaneously or laparoscopically through tissue without an introducer. Introducer electrode 14 combines the function of an introducer and an electrode. Introducer electrode 14 can have a sharpened distal end 14' to assist introduction through tissue. At least a portion of distal end 14' is uninsulated and is an electrode. Each secondary electrode 16 has a distal end 16' that is constructed to be less structurally rigid than introducer electrode 14. Distal end 16' is that section of secondary electrode 16 that is advanced from the lumen of introducer electrode 14 and into the selected tissue mass. Distal end is typically less structurally rigid that introducer electrode 14. However, even though sections of secondary electrode 16 which are not advanced through the selected tissue mass may be less structurally rigid than introducer electrode 14.

Structural rigidity is determined by, (i) choosing different materials for introducer electrode 14 and distal end 16' or some greater length of secondary electrode 16, (ii) using the same material but having less of it for secondary electrode 16 or distal end 16', e.g., secondary electrode 16 or distal end 16' is not as thick as introducer electrode 14, or (iii) including another material in one of the electrodes 14 or 16 to vary their structural rigidity. For purposes of this disclosure, structural rigidity is defined as the amount of deflection that an electrode has relative to its longitudinal axis. It will be appreciated that a given electrode will have different levels of rigidity depending on its length.

Introducer and secondary electrodes 14 and 16 can be made of a variety of conductive materials, both metallic and non-metallic. One suitable material is type 304 stainless steel of hypodermic quality.

Figure 2:
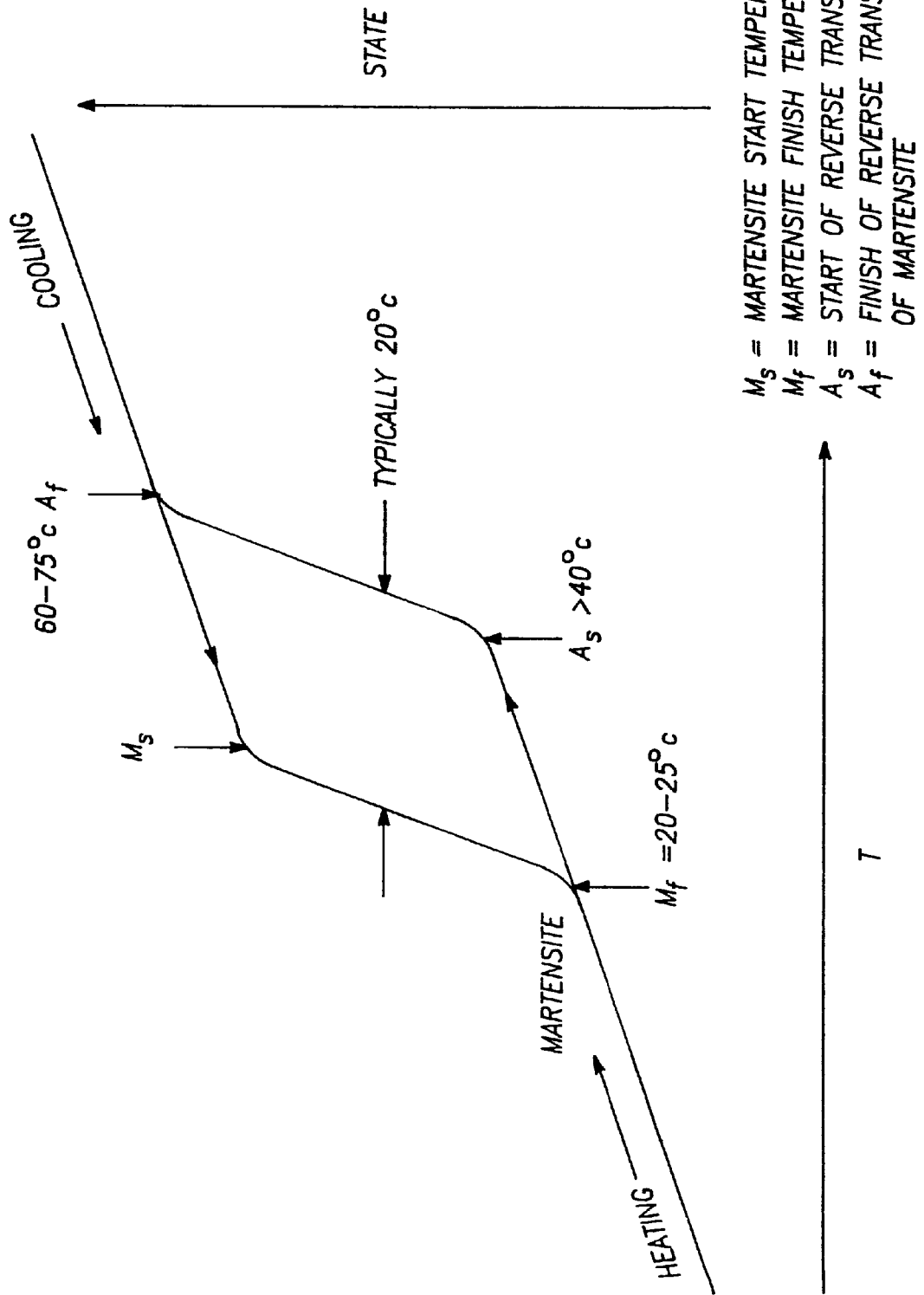
FIG. 2 illustrates the stress-strain behavior of an alloy which exhibits stress-induced martensite behavior above body temperature.

At least a portion of distal portion of secondary electrodes 16 is made of a shaped alloy material that exhibits stress induced martensite behavior above body tempeature, as illustrated in FIG. 2. The selected shaped memory alloy material has transtion temperatures that during positioning of introducer electrode 14 secondary electrodes 16 are in a non-stressed induced martensite state. A $M_f$ is in the range of 20 to 25 degrees C, which is substantially at or above room temperature, and an $A_s$ greater than 40 degrees C, which is substantially greater than body temperature. This allows for the shaped memory alloy to remain in a fully martensite state during the positioning of introducer electrode 14. Introducer electrode 14 does not constrain secondary electrodes 16. Before secondary electrodes 16 are introduced into tissue, energy is applied to the distal portion of introducer electroder 14, which delivers heat to secondary electrodes 16. A transition temperature of $A_f$ of 60 to 75 degrees C is used as the temerature as at which introducer electrode 14 must achieve before secondary electrodes 16 can be deployed in tissue.

Each of introducer or secondary electrodes 14 or 16 can have different lengths. The lengths can be determined by the actual physical length of an electrode, the amount of an electrode that has an ablation delivery surface, and the length of an electrode that is not covered by an insulator. Suitable lengths include but are not limited to 17.5 cm, 25.0 cm. and 30.0 cm. The actual length of an electrode depends on the location of the selected tissue mass to be ablated, its distance from the skin, its accessibility as well as whether or not the physician chooses a laproscopic, percutaneous or other procedure. Further, ablation treatment apparatus 10, and more particularly multiple electrode device 12, can be introduced through a guide to the desired tissue mass site.

An insulation sleeve 18 may be positioned around an exterior of one or both of the introducer and secondary electrodes 14 and 16 respectively. Preferably, each insulation sleeve 18 is adjustably positioned so that the length of an electrode ablation surface can be varied. Each insulation sleeve 18 surrounding an introducer electrode 14 can include one or more apertures. This permits the introduction of a secondary electrode 16 through introducer electrode 14 and insulation sleeve 18.

In one embodiment, insulation sleeve 18 can comprise a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Introducer electrode 14 is made of a stainless-steel hypodermic tubing with 2 cm of exposed ablation surface. Secondary electrodes 16 have distal ends 16' that are made of NiTi hypodermic tubing. A handle is included with markings to show the varying distance of secondary electrodes 16 from introducer electrode 14. Fluid infusion is delivered through a Luer port at a side of the handle. Type-T thermocouples are positioned at distal ends 16'.

An energy source 20 is connected to multiple electrode device 12 with one or more cables 22. Energy source 20 can be an RF source, microwave source, short wave source, laser source and the like. Multiple electrode device 12 can be comprised of introducer and secondary electrodes 14 and 16 that are RF electrodes, microwave antennas, as well as combinations thereof. Energy source 20 may be a combination RF/microwave box. Further a laser optical fiber, coupled to a laser source 20 can be introduced through one or both of introducer or secondary electrodes 14 and 16. One or more of the introducer or secondary electrodes 14 and 16 can be an arm for the purposes of introducing the optical fiber.

Electrodes 14 and 16 may be electromagnetically coupled by wiring, soldering, connection to a common couplet, and the like. This permits only one electrode 14 or 16 to be coupled to energy source 20 and use of a single cable 22.

One or more sensors 24 may be positioned on interior or exterior surfaces of introducer electrode 14, secondary electrode 16 or insulation sleeve 18. Preferably sensors 24 are positioned at introducer electrode distal end 14', secondary electrode distal end 16' and insulation sleeve distal end 18'. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at energy source 20 which then regulates the amount of energy delivered to introducer and/or secondary electrodes 14 and 16.

Thus the geometry of the ablated mass is selectable and controllable. Any number of different ablation geometries can be achieved. This is a result of having variable lengths for introducer electrode 14 and secondary electrode 16 ablation surfaces as well as the inclusion of sensors 24.

Preferably, distal end 16' is laterally deployed relative to a longitudinal axis of introducer electrode 14 out of an aperture 26 formed in introducer electrode 14. Aperture 26 is at distal end 14' or formed in a side of an exterior of electrode 14.

A method for creating an ablation volume in a selected tissue mass includes inserting and advancing introducer electrode 14 through tissue and into a selected tissue mass. Secondary electrodes 16 are positioned in a lumen formed in introducer electrode 14 while introducer electrode 14 is advanced through tissue. At least one distal end 16' is deployed from the introducer electrode lumen into the selected tissue mass in a lateral direction relative to the longitudinal axis of introducer electrode 14. Electromagnetic energy is delivered from one of an introducer electrode ablation surface, a secondary electrode ablation surface or both to the selected tissue mass. An ablation volume is created in the selected tissue mass. When operated in the monopolar mode, the ablation is between the ablation surfaces of the electrodes.

There is wide variation in the amount of deflection of secondary electrode 16. For example, secondary electrode 16 can be deflected a few degrees from the longitudinal axis of introducer electrode 14, or secondary electrode can be deflected in any number of geometric configurations, including but not limited to a "J" hook. Further, secondary electrode 16 is capable of being introduced from introducer electrode 14 a few millimeters from introducer electrode, or a much larger distance. Ablation by secondary electrode 16 can begin a few millimeters away from introducer electrode 14, or secondary electrode 16 can be advanced a greater distance from introducer electrode 14 and at that point the initial ablation by secondary electrode 16 begins.

Figure 3A:
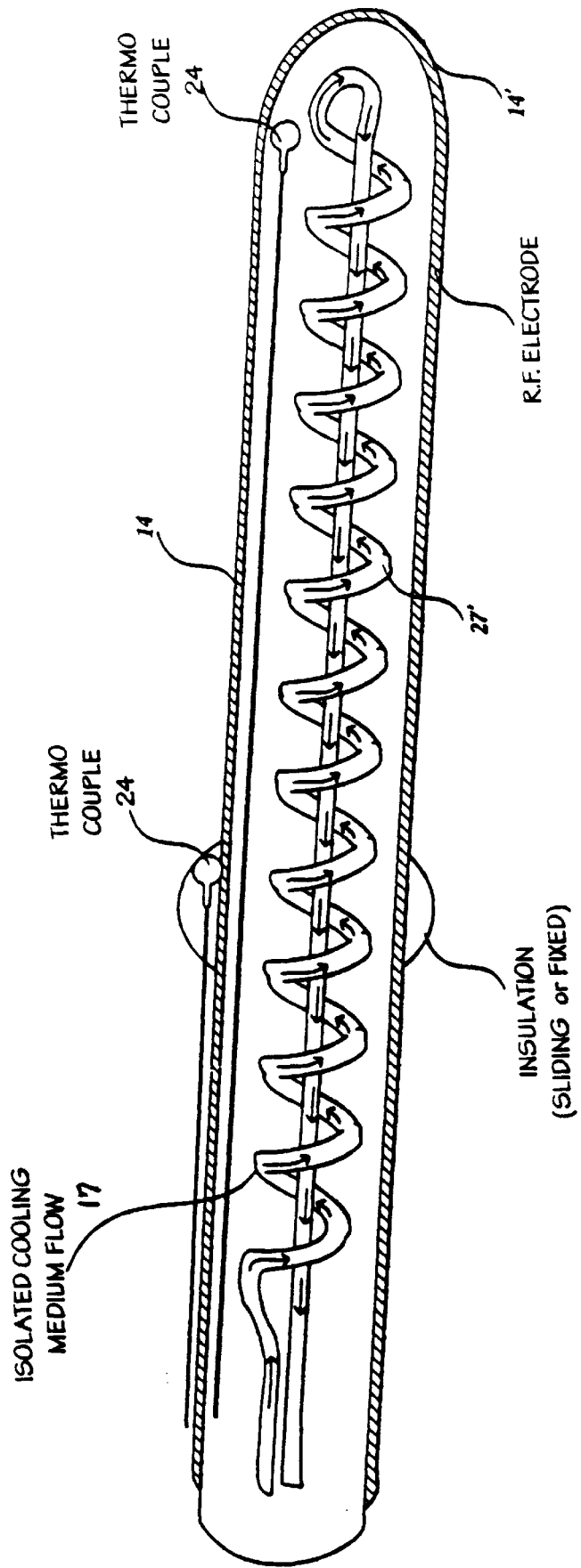
FIG. 3(a) is a cross-sectional view of the introducer electrode with a closed distal end and a cooling element positioned in a central lumen of the introducer electrode.

As illustrated in FIG. 3(a), introducer electrode 14 can include one or more cooling elements 27. One embodiment of a suitable cooling element 27 is a closed elongated structure 27' coupled to a circulating system to introduce a cooling medium. Two lumens can be incorporated with introducer electrode 14, or secondary electrode 16, to carry a cooling medium to and away from electrodes 14 or 16. In one embodiment, the dimensions of the lumens are: outer lumen 0.117 inches outer diameter by 0.088 inches inner diameter, and inner lumen 0.068 inches outer diameter by 0.060 inner diameter. The cooling medium enters introducer electrode 14, absorbs heat generated in the tissue surrounding introducer electrode 14, and the heated medium then exits introducer electrode 14. This may be achieved by the use of the two lumens, one introducing the cooling medium, and the other lumen removing heated cooling solution. Heat is subsequently removed from the heated medium, and once again cooled medium is recirculated through introducer electrode 14. This is a continuous process. Cooling element 27 need only be positioned and provide the cooling function, along that section of introducer electrode 14 which has an ablation energy delivery surface. Insulation sleeve 18 can be slideably adjustable along the length of introducer electrode 14 or be in a fixed positioned. The exterior of introducer electrode 14 which is not covered by insulation sleeve 18 provides the ablation energy delivery surface. It is only this surface which becomes heated and charred from electromagnetic energy delivered to adjacent tissue. Thus it is only necessary to cool this surface of introducer electrode 14, and the actual cooling by cooling medium 17 can be limited to the ablation energy delivery surface.

Cooling medium may be a refrigerant including but not limited to ethyl alcohol, freon, polydimethisiloxane, and the like. Cooling can also be achieved with gas expansion cooling by the Joule-Thompson effect.

In another embodiment of cooling element 27, distal end 14' is again closed, and a cooling medium 27 flows through the central lumen formed in introducer electrode 14. The cooling medium 27 is coupled to a recirculation system, which may be a heat exchanger with a pump. The rate of fluid flow through introducer electrode 14 is variable based on a number of different parameters.

Figure 3B:
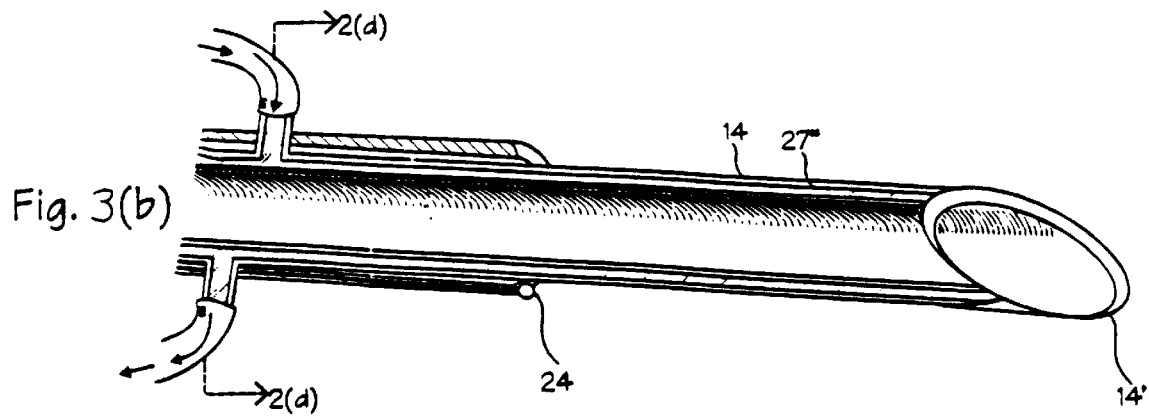
FIG. 3(b) is a cross-sectional view of the introducer electrode with an open distal end and an elongated cooling element positioned in the central lumen of the introducer electrode.
Figure 3C:
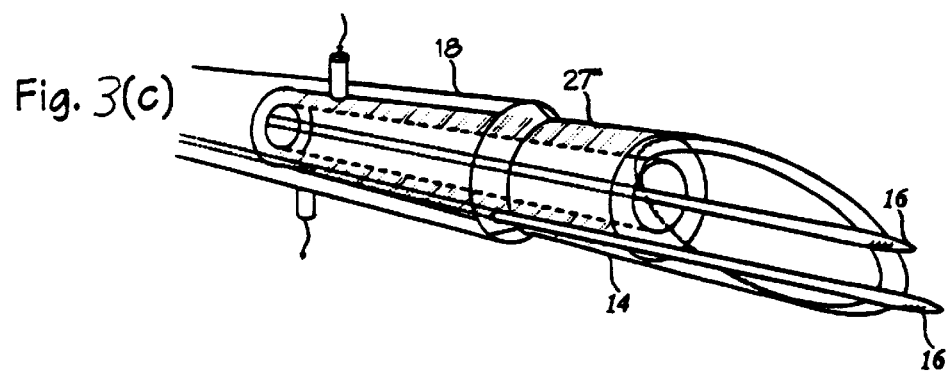
FIG. 3(c) is distal end view of the apparatus of FIG. 3(b).

In yet another embodiment, cooling element 27 is an elongated structure 27", including but not limited to a tubular member such as a cylinder, with a cooling medium flowing through elongated structure 27" (FIG. 3(b)). Elongated structure 27" is positioned within the central lumen of introducer electrode 14 and can extend to distal end 14'. Distal end 14' can be open or closed. Cooling medium is confined within elongated structure 27". This permits the introduction and flow of other mediums through the hollow lumen of introducer electrode 14. Secondary electrodes 16 can exit at distal end 14', or alternatively, they may also exit along a side of introducer electrode 14 (FIG. 3(c)).

Figure 3D:
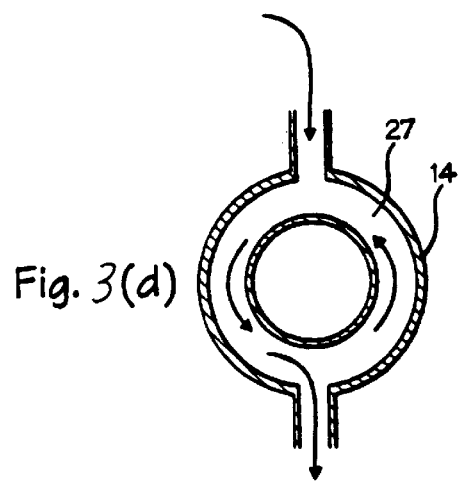
FIG. 3(d) is a cross-sectional view of the apparatus of FIG. 3(b) taken along the lines 2(d)—2(d).

Cooling medium flow through cooling element 27 can introduced through a first port, and exit through a second port (FIG. 3(d)).

A variety of different cooling mediums can be used including but not limited to gas, cooled air, refrigerated air, compressed air, freon, water, alcohol, and the like. Additionally, cooling element 27 can be incorporated into the walls defining introducer electrode 14, and may also be positioned at the exterior of introducer electrode 14. The desired cooling affect can be achieved without recirculation of the cooling medium. A chiller can also be utilized. The combination of flow rate of cooling medium and temperature is important to achieve a desired level of cooling.

As the amount of cooling increases, the more RF energy effects can be distributed over a larger area. Cooling is provided and controlled until the end of the ablation, at which time the tissue adjacent to electrodes 14 and 16 is then ablated. The RF radiation effect on tissue is controlled by the cooling conductive effect.

Cooling element 27 can also be included with secondary electrodes 16, as implemented with introducer electrode 14.

Electromagnetic energy delivered through introducer or secondary electrodes 14 or 16 causes the tissue adjacent to the electrode with the ablation energy delivery surface to heat, and return the heat to the electrode 14 and 16. As more heat is applied and returned, the charring effect of electrode 14 and 16 increases. This can result in a loss of electromagnetic energy conductivity through electrodes 14 and 16. The inclusion of cooling element 27 does not affect the effective delivery of electromagnetic energy to a targeted mass. Cooling element 27 permits the entire targeted mass to be ablated while reducing or eliminating the heating of adjacent tissue to electrodes 14 and 16. Cooling is only necessary where there is an exposed electrode 14 and 16 surface.

Figure 4:
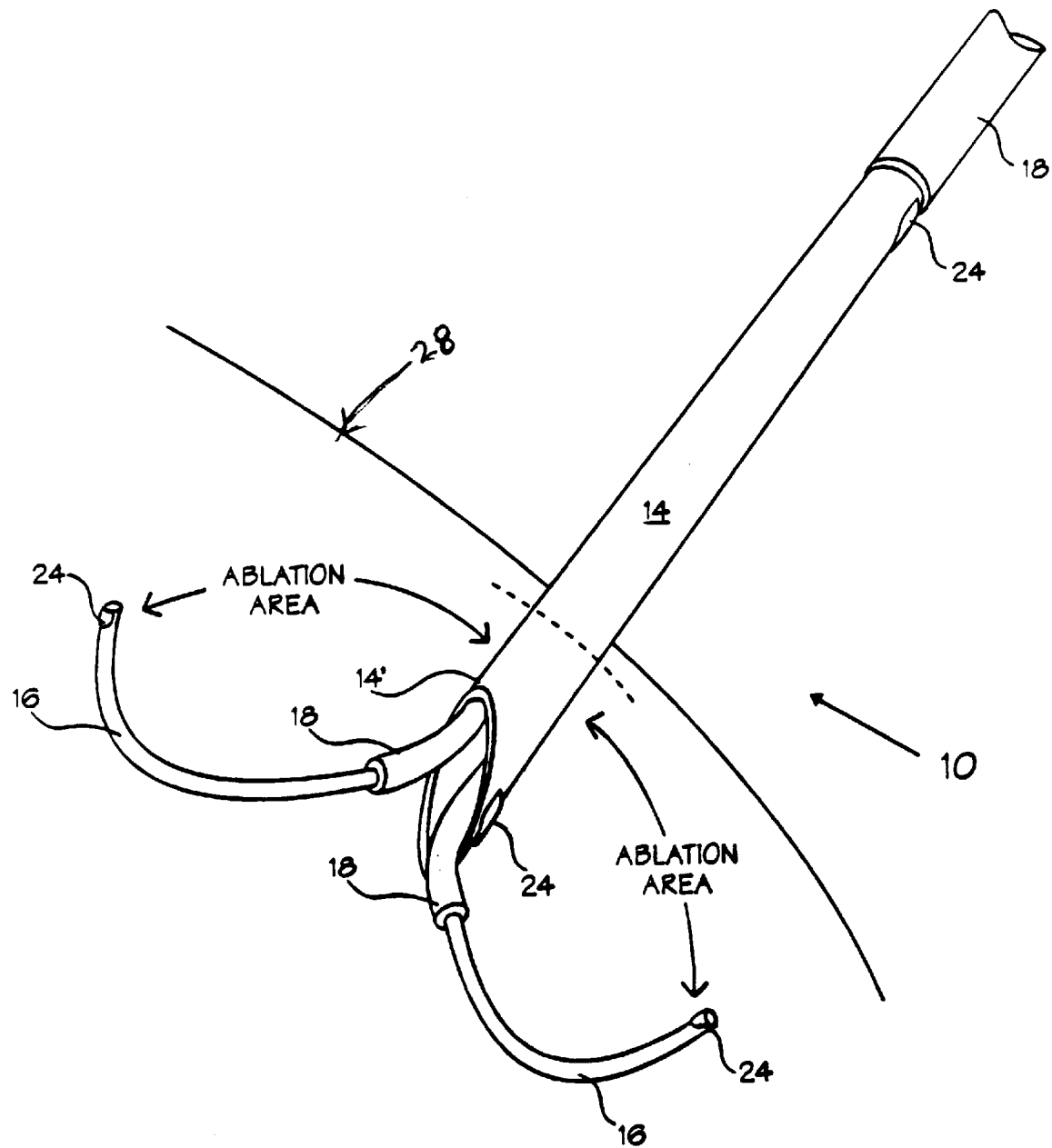
FIG. 4 is a perspective view of the ablation apparatus of the present invention with two secondary electrodes deployed into the selected tissue mass.

In FIG. 4, two secondary electrodes 16 are each deployed out of distal end 14' and introduced into selected tissue mass 28. Secondary electrodes 16 form a plane and the area of ablation extends between the ablation surfaces of introducer and secondary electrodes 14 and 16. Introducer electrode 14 can be introduced in an adjacent relationship to selected tissue mass 28. This particular deployment is particularly useful for small selected tissue masses 28, or where piercing selected tissue mass 28 is not desirable. Introducer electrode 14 can be rotated, with secondary electrodes 16 retracted into a central lumen of introducer electrode 14, and another ablation volume defined between the two secondary electrodes 16 is created. Further, introducer electrode 14 can be withdrawn from its initial position adjacent to selected tissue mass 28, repositioned to another position adjacent to selected tissue mass 28, and secondary electrodes 16 deployed to begin another ablation cycle. Any variety of different positionings may be utilized to create a desired ablation geometry for selected tissue mass of different geometries and sizes.

Figure 5:
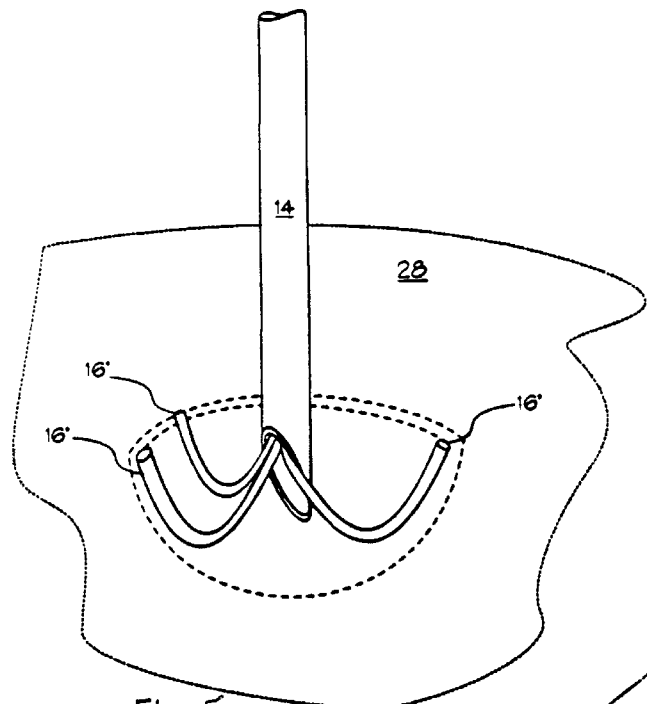
FIG. 5 is a perspective view illustrating the ablation created by the introduction of three secondary electrodes into the selected tissue mass.

In FIG. 5, three secondary electrodes 16 are introduced into selected tissue mass 28. The effect is the creation of an ablation volume without leaving non-ablated areas between electrode ablation surfaces. The ablation is complete.

Figure 6:
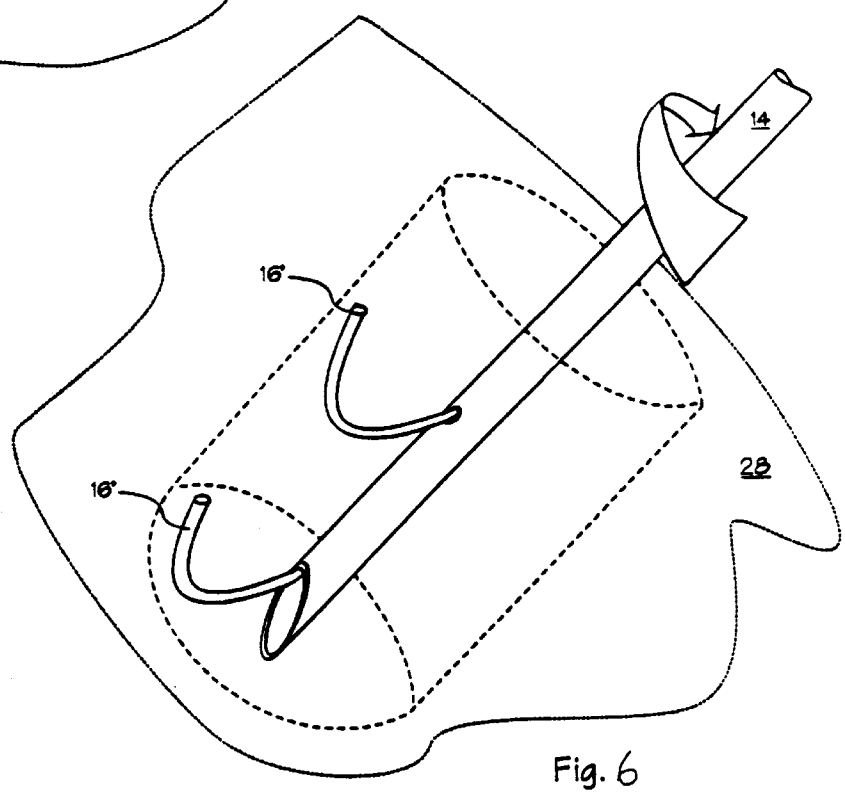
FIG. 6 is a perspective view illustrating the positioning of the multiple electrode ablation apparatus in the center of a selected tissue mass, and the creation of a cylindrical ablation.

Referring now to FIG. 6, a center of selected tissue mass 28 is pierced by introducer electrode 14, secondary electrodes 16 are laterally deployed and retracted, introducer electrode 14 is rotated, secondary electrodes 16 are deployed and retracted, and so on until a cylindrical ablation volume is achieved. Multiple electrode device 12 can be operated in the bipolar mode between the two secondary electrodes 16, or between a secondary electrode 16 and introducer electrode 14. Alternatively, multiple electrode device 12 can be operated in a monopolar mode.

Secondary electrodes 16 can serve the additional function of anchoring multiple electrode device 12 in a selected mass, as illustrated in FIGS. 7(a) and 7(b). In FIG. 7(a) one or both secondary electrodes 16 are used to anchor and position introducer electrode 14. Further, one or both secondary electrodes 16 are also used to ablate tissue. In FIG. 7(b), three secondary electrodes are deployed and anchor introducer electrode 14.

FIG. 7(c) illustrates the infusion capability of multiple electrode device 12. Three secondary electrodes 16 are positioned in a central lumen 14" of introducer electrode 14. One or more of the secondary electrodes 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent.

Figure 9:
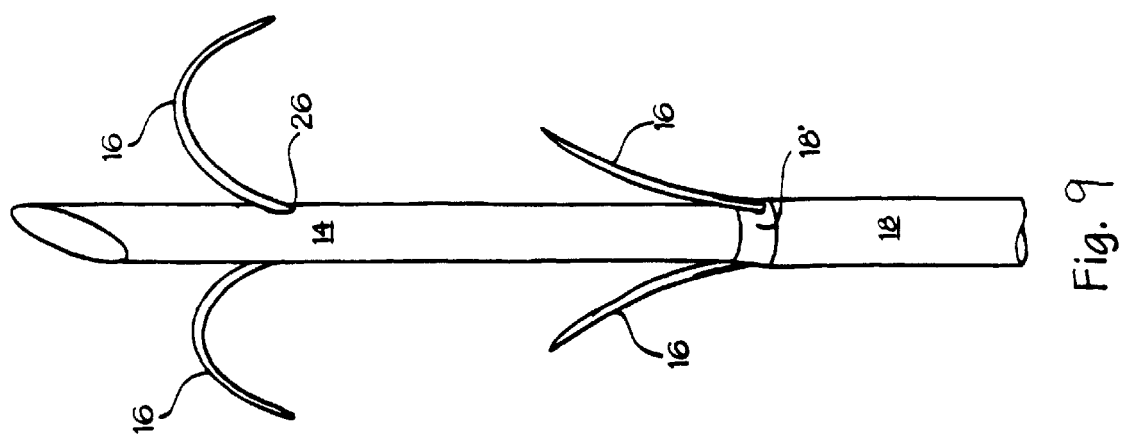
FIG. 9 is a perspective view of the multiple electrode ablation apparatus of the present invention illustrating the deployment of two secondary electrodes from the introducer electrode, and the deployment of three secondary electrodes from the distal end of the insulation sleeve surrounding the introducer electrode.
Figure 8:
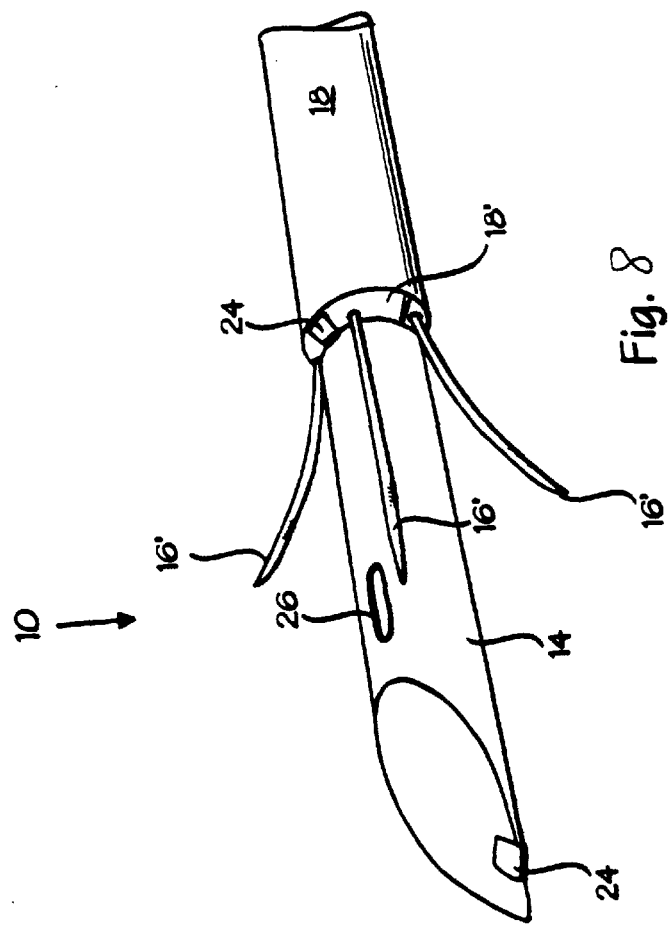
FIG. 8 is a perspective view of the multiple electrode ablation apparatus of the present invention illustrating the deployment of three secondary electrodes from a distal end of the insulation sleeve surrounding the introducer electrode.

As shown in FIG. 8, insulation sleeve 18 can include one or more lumens for receiving secondary electrodes 16 which are deployed out of an insulation sleeve distal end 18'. FIG. 9 illustrates three secondary electrodes 16 being introduced out of insulation sleeve distal end 18', and two secondary electrodes 16 introduced through apertures 26 formed in introducer electrode 14. As illustrated, the secondary electrodes introduced through apertures 26 provide an anchoring function. It will be appreciated that FIG. 9 shows that secondary electrodes 16 can have a variety of different geometric configurations in multiple electrode device 12.

A feedback control system 29 is connected to energy source 20, sensors 24 and electrodes 14 and 16. Feedback control system 29 receives temperature or impedance data from sensors 24 and the amount of electromagnetic energy received by electrodes 14 and 16 is modified from an initial setting of electromagnetic energy output, ablation time, temperature, and current density (the "Four Parameters"). Feedback control system 29 can automatically change any of the Four Parameters. Feedback control system 29 can detect an impedance or temperature and change any of the Four Parameters. Feedback control system can include a multiplexer to multiplex different electrodes, a temperature detection circuit that provides a control signal representative of temperature or impedance detected at one or more sensors 24. A microprocessor can be connected to the temperature control circuit.

The following discussion pertains particularly to the use of an RF energy source and RF multiple electrode device 12. It will be appreciated that devices similar to those associated with RF multiple electrode device 12 can be utilized with laser optical fibers, microwave devices and the like.

Referring now to FIG. 10, all or portions of feedback control system 29 are illustrated. Current delivered through introducer and secondary electrodes 14 and 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at the respective introducer and/or secondary electrodes 14 and 16.

In a similar manner, temperatures detected at sensors 24 provide feedback for maintaining a selected power. The actual temperatures are measured at temperature measurement device 42, and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and electromagnetic energy is delivered between introducer electrode 14 and secondary electrodes 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at introducer and secondary electrodes 14 and 16. The amount of RF energy delivered controls the amount of power. A profile of power delivered can be incorporated in controller 38, and a preset amount of electromagnetic energy to be delivered can also be profiled.

Circuitry, software and feedback to controller 38 result in process control, and the maintenance of the selected power that is independent of changes in voltage or current, and are used to change, (i) the selected power, including RF, microwave, laser and the like, (ii) the duty cycle (on-off and wattage), (iii) bipolar or monopolar electromagnetic energy delivery and (iv) infusion medium delivery, including flow rate and pressure of the cooling and infusion mediums. These process variables are controlled and varied, while maintaining the desired delivery of power based on temperatures monitored at sensors 24.

Figure 11:
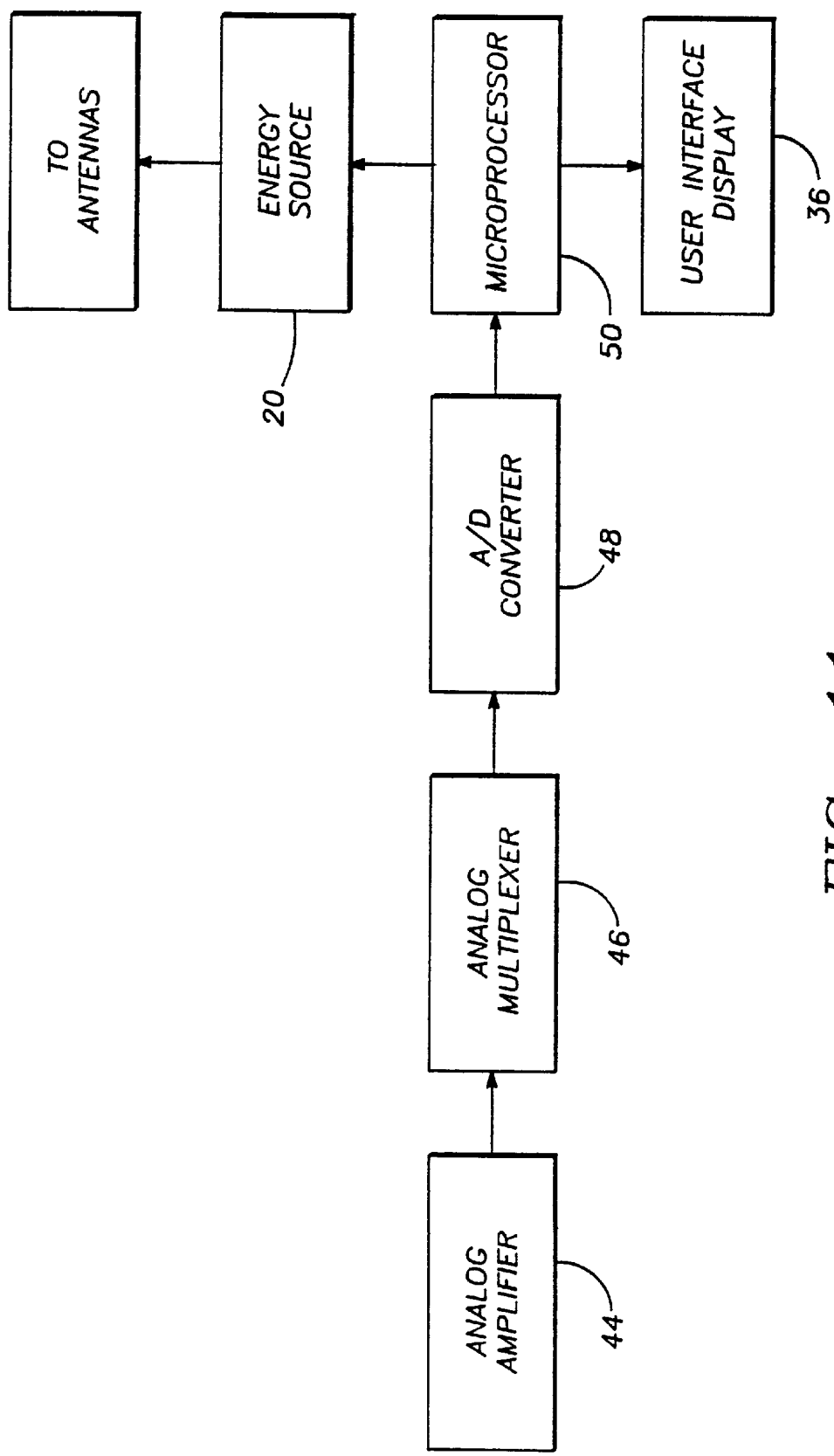
FIG. 11 is a block diagram illustrating an analog amplifier, analog multiplexer and microprocessor used with the present invention.

Referring now to FIG. 11, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36. The delivery of RF energy can be reduced, modified or interrupted. A control signal from microprocessor 50 can modify the power level supplied by power source 36.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation apparatus, comprising:
    an introducer including with a distal end sufficiently sharp to penetrate tissue;

an energy delivery device configured to be coupled to an energy source, the energy delivery device including a first electrode and a second electrode each having a tissue piercing distal portion, the first and second electrodes being at least partially positionable in the introducer and deployable from the introducer at a selected tissue site to an expanded state of deployed first and second electrodes that distend laterally away from the introducer with a radius of curvature to form a shaped array of deployed electrodes at the tissue site when positioned at the selected tissue site, wherein the first electrode distal portion and the second electrode distal portion are each at least partially made of a shaped memory alloy material that displays stress induced martensite behavior above body temperature; and a cable coupling the energy source to the energy delivery device.

2. The apparatus of claim 1, wherein a distal portion of the introducer is an electrode.

3. The apparatus of claim 1, further comprising:

an electrode advancement and retraction member coupled to the first and second electrodes.

4. The apparatus of claim 1, wherein the first and second electrodes are retractable in and out of the introducer.

5. The apparatus of claim 1, wherein each of the first and second electrodes has a tissue piercing distal end.

6. The apparatus of claim 1, wherein the first and second electrodes are in a non-stress induced martensite state when positioned in the introducer prior to deployment at the selected tissue site.

7. The apparatus of claim 1, wherein the shaped memory alloy material displays stress induced martensite behavior at a tempeature greater than 40 degrees C.

8. The apparatus of claim 1, wherein the first and second electrodes are in a non-restrained state when positioned in the introducer prior to deployment at the selected tissue site.

9. The apparatus of claim 1, further comprising:

a first sensor coupled to the first electrode.

10. The apparatus of claim 9, wherein the first sensor is positioned at the distal portion of the first electrode.

11. The apparatus of claim 9, wherein the first sensor is a temperature sensor.

12. The apparatus of claim 9, wherein the first sensor an impedance sensor.

13. The apparatus of claim 9, further comprising:

a second sensor.

14. The apparatus of claim 13, wherein the second sensor is positioned at the distal portion of the second electrode.

15. The apparatus of claim 13, wherein the second sensor is a thermal sensor.

16. The apparatus of claim 13, wherein the second sensor is an impedance sensor.

17. The apparatus of claim 9, further comprising:

a feedback control system coupled to the first sensor.

18. The apparatus of claim 17, wherein the feedback control system is responsive to a detected characteristic from the first sensor and provides a delivery of ablation energy output from the energy source to the first and second electrodes.

19. The apparatus of claim 13, further comprising:

a feedback control system coupled to the second sensor.

20. The apparatus of claim 19, wherein the feedback control system is responsive to a detected characteristic from the second sensor and provides a delivery of ablation energy output from the energy source to the first and second electrodes.

21. The apparatus of claim 2, wherein the introducer has an energy delivery surface with a length that is at least 20% of a length of an energy delivery surface of the first electrode.

22. The apparatus of claim 2, wherein the introducer has an energy delivery surface with a length that is at least one-third of a length of an energy delivery surface of the first electrode.

23. The apparatus of claim 2, wherein the introducer has an energy delivery surface with a length that is at least one-half of a length of an energy delivery surface of the first electrode.

24. The apparatus of claim 1, wherein the shaped memory alloy material is an alloy of nickel titanium.

25. The apparatus claim 1, further comprising:

a third electrode, wherein the third electrode distal portion is at least partially made of a shaped memory alloy material that displays stress induced martensite behavior above body temperature.

26. The apparatus of claim 25, wherein the first, second and third electrodes are retractable electrodes.

27. The apparatus of claim 26, wherein the retractable electrodes advance from the introducer and deploy in a lateral direction away from a periphery of the introducer and define a three dimensional ablation volume between the deployed retractable electrodes, each of the retractable electrodes in a deployed state exhibiting at least one radius of curvature outside of and away from the introducer to define the three dimensional ablation volume.

28. The apparatus of claim 1, further comprising:

an insulation sleeve positioned in a surrounding relationship around at least a portion of an exterior of the introducer.

29. The apparatus of claim 28, wherein the insulation sleeve is adjustably moveable along an exterior of the introducer.

30. The apparatus of claim 1, further comprising:

an insulation sleeve positioned in a surrounding relationship around at least a portion of an exterior of the first and second electrodes.

31. The apparatus of claim 1, further comprising:

a ground pad electrode.

32. The apparatus of claim 1, wherein the first and second electrodes are RF electrodes.

33. The apparatus of claim 2, wherein the first and second electrodes are operated in a monopolar mode.

34. The apparatus of claim 2, wherein the first and second electrodes are operated in a bipolar mode.

35. The apparatus of claim 1, wherein the first electrode is hollow and configured to be coupled to an infusion medium source.

36. A method for creating an ablation volume in a selected tissue mass, comprising:

providing an ablation apparatus including an introducer, an energy source, a first electrode and a second electrode at least partially positionable in the introducer, wherein a first electrode distal portion and a second electrode distal portion are each at least partially made of a shaped memory alloy material that displays stress induced martensite behavior above body temperature;

advancing the introducer through tissue to the selected tissue site;

applying energy to the first and second electrode distal portions while positioned in the introducer and creating a stress induced martensitic state in the first and second electrodes at a temperature above body temperature;

advancing the first and second electrodes from the introducer to surround a selected tissue mass;

delivering energy from the energy source to the first and second electrodes; and creating an ablation volume in the selected tissue mass.

37. The method of claim 36, wherein a distal portion of the introducer is an electrode and the ablation volume is defined by the first and second electrodes and the distal portion of the introducer.

38. The method of claim 36, wherein the first and second electrodes are in a non-stress induced martensitic state when positioned in the introducer prior to deployment at the selected tissue site.

39. The method of claim 36, wherein the shaped memory alloy material displays stress induced martensite behavior at a tempeature greater than 40 degrees C.

40. The method of claim 36, wherein the first and second electrodes are in a non-restrained state when positioned in the introducer prior to deployment at the selected tissue site.

41. The method of claim 36, further comprising:

measuring a temperature with a first sensor coupled to the first electrode.

42. The method of claim 41, wherein the temperature is measured at a periphery of the selected tissue site.

43. The method of claim 41, wherein the temperature is measured outside of a periphery of the selected tissue site.

44. The method of claim 36, further comprising:

measuring an impedance at the selected tissue site after energy is delivered to the selected tissue site.

45. The method of claim 36, wherein the shaped memory alloy material is an alloy of nickel titanium.

46. The method of claim 36, wherein the apparatus further includes a third electrode, wherein the third electrode distal portion is at least partially made of a shaped memory alloy material that displays stress induced martensite behavior above body temperature.

47. The method of claim 46, wherein the first, second and third electrodes are advance from the introducer and deployed in a lateral direction away from a periphery of the introducer and define a three dimensional ablation volume between the deployed retractable electrodes, each of the retractable electrodes in a deployed state exhibiting at least one radius of curvature outside of and away from the introducer to define the three dimensional ablation volume.

48. The method of claim 47, wherein the first, second and third electrodes are RF electrodes.

* * * * *